(12) United States Patent
Pooler

(10) Patent No.: US 7,810,241 B2
(45) Date of Patent: Oct. 12, 2010

(54) SHIELDED SCALPEL

(76) Inventor: Jason C. Pooler, 3708 Lerch St., Chattanooga, TN (US) 37411

( * ) Notice: Subject to any disclaimer, the term of this patent is extended or adjusted under 35 U.S.C. 154(b) by 806 days.

(21) Appl. No.: 11/419,773

(22) Filed: May 23, 2006

(65) Prior Publication Data
US 2007/0276422 A1 Nov. 29, 2007

(51) Int. Cl.
B26B 3/06 (2006.01)
A61B 17/32 (2006.01)

(52) U.S. Cl. .................. 30/151; 30/286; 606/167
(58) Field of Classification Search ............ 30/151, 30/153, 286, 2, 143; 606/167
See application file for complete search history.

(56) References Cited

U.S. PATENT DOCUMENTS

| 1,452,893 A * | 4/1923 | Porth .............. 30/286 |
| 4,719,915 A | 1/1988 | Porat et al. |
| 4,980,977 A * | 1/1991 | Matin et al. .......... 30/286 |
| 5,071,426 A | 12/1991 | Dolgin et al. |
| 5,116,351 A | 5/1992 | Frassetti |
| 5,139,507 A | 8/1992 | Dolgin et al. |
| 5,250,063 A | 10/1993 | Abidin et al. |
| 5,250,064 A * | 10/1993 | Schneider ............ 606/167 |
| 5,275,606 A | 1/1994 | Abidin et al. |
| 5,299,357 A | 4/1994 | Wonderley et al. |
| 5,309,641 A | 5/1994 | Wonderley et al. |
| 5,330,492 A | 7/1994 | Haugen |
| 5,342,379 A | 8/1994 | Volinsky |
| 5,411,512 A | 5/1995 | Abidin et al. |
| 5,417,704 A | 5/1995 | Wonderley |
| 5,470,339 A | 11/1995 | Lerrick |
| 5,527,329 A | 6/1996 | Gharibian |
| 5,569,281 A | 10/1996 | Abidin et al. |
| 5,620,454 A | 4/1997 | Pierce et al. |
| 5,730,751 A | 3/1998 | Dillon et al. |
| 5,919,201 A | 7/1999 | Carter et al. |
| 5,938,675 A | 8/1999 | Gharibian |
| 5,938,676 A | 8/1999 | Cohn et al. |
| 5,941,892 A | 8/1999 | Cohn et al. |
| 6,015,419 A | 1/2000 | Strome et al. |
| 6,718,637 B1 * | 4/2004 | Ortner et al. ............ 30/2 |
| 2003/0093905 A1 | 5/2003 | Dambal et al. |
| 2003/0105479 A1 | 6/2003 | Pilo et al. |
| 2004/0015104 A1 | 1/2004 | Goldberger |
| 2004/0215174 A1 | 10/2004 | Morawski et al. |

* cited by examiner

Primary Examiner—Stephen Choi
(74) Attorney, Agent, or Firm—Hahn Loeser & Parks, LLP; Keith J. Marcinowski

(57) ABSTRACT

A scalpel is provided with a shield that is detachably connected to the handle of the scalpel and covers the blade of the scalpel. The scalpel includes a sliding assembly disposed on a portion of the handle of the scalpel. Movement of the sliding assembly causes the shield to rotate between a first position and a second position, wherein the blade is at least partially exposed.

17 Claims, 10 Drawing Sheets

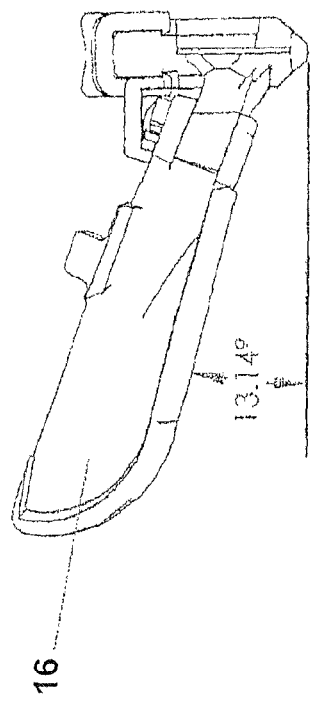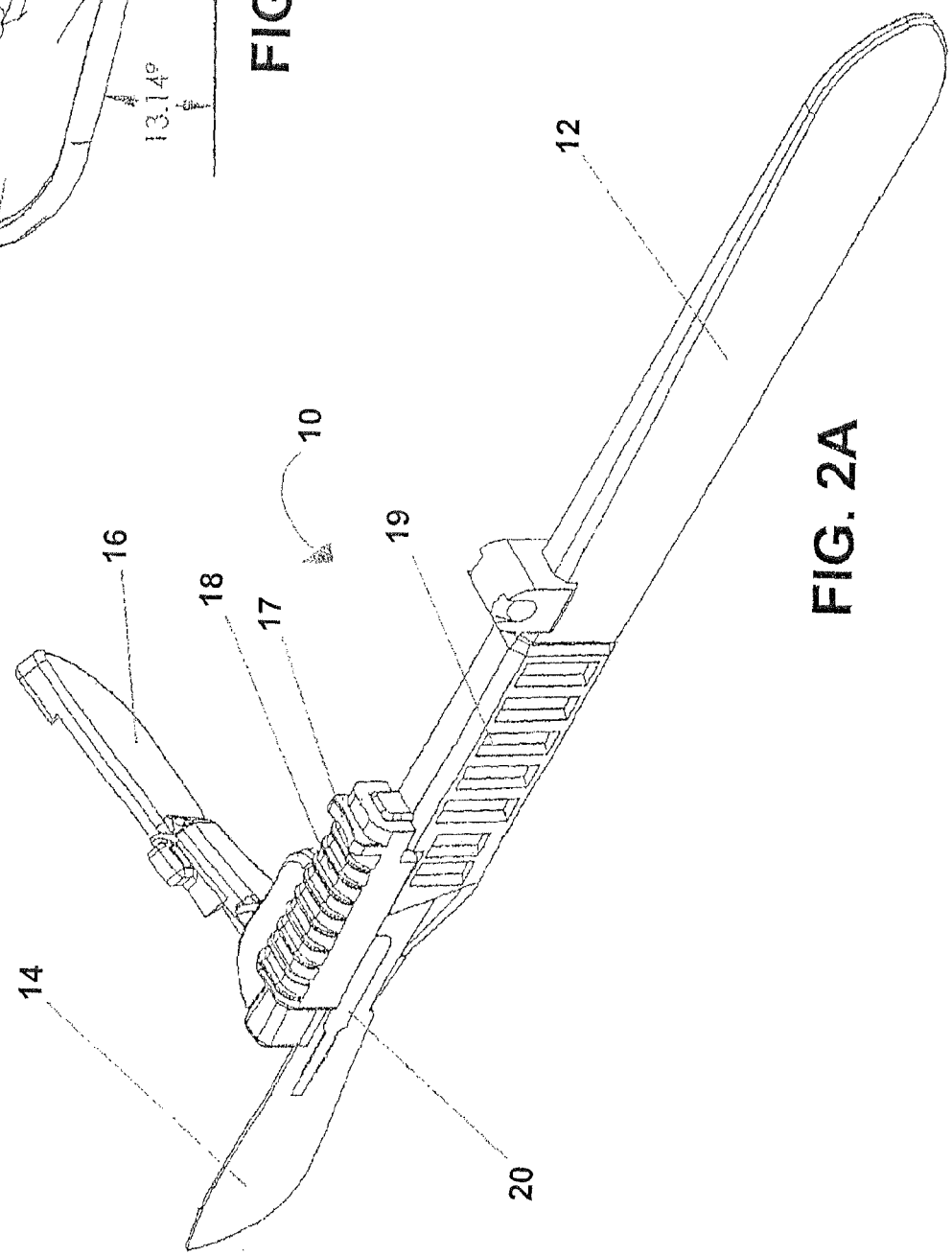

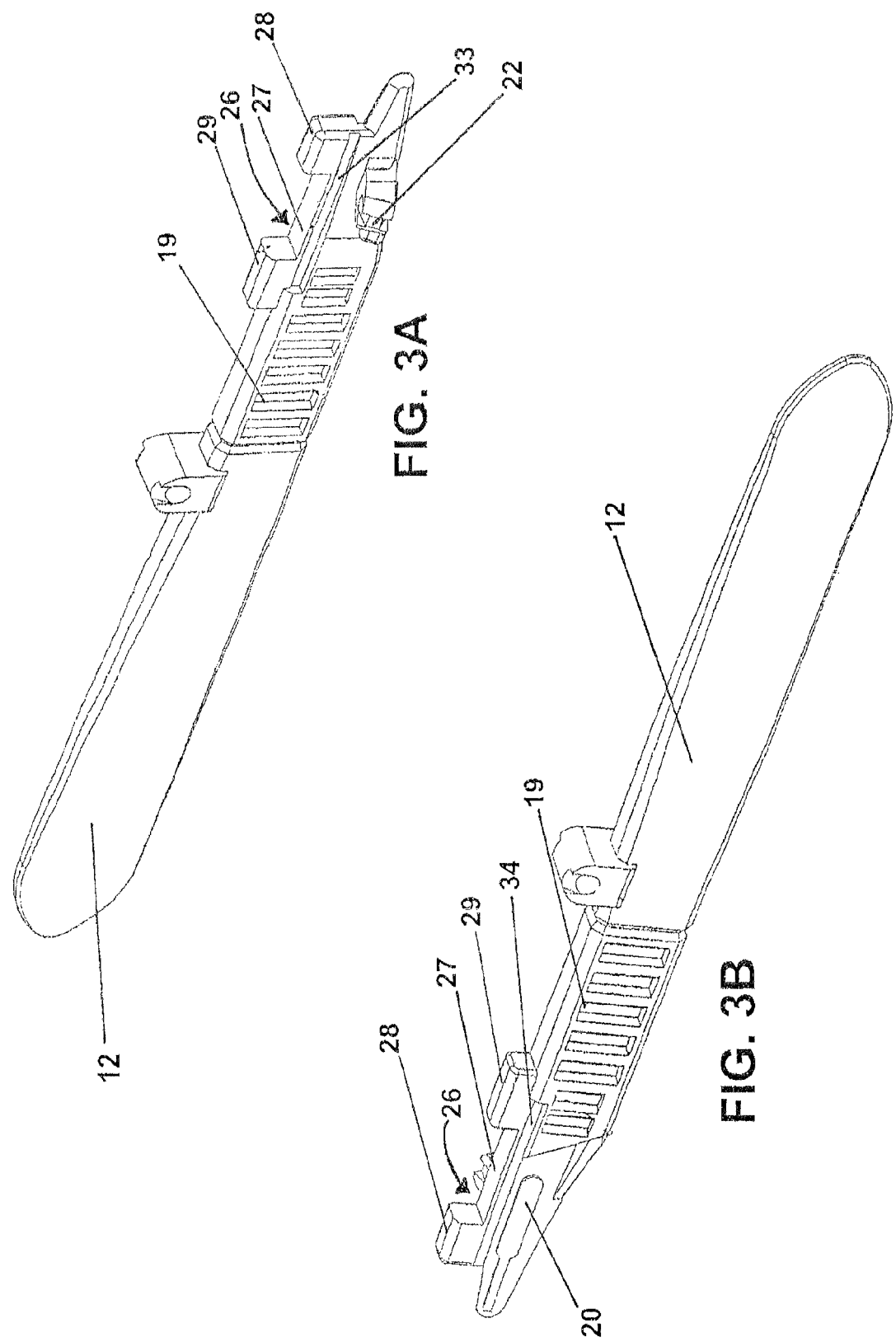

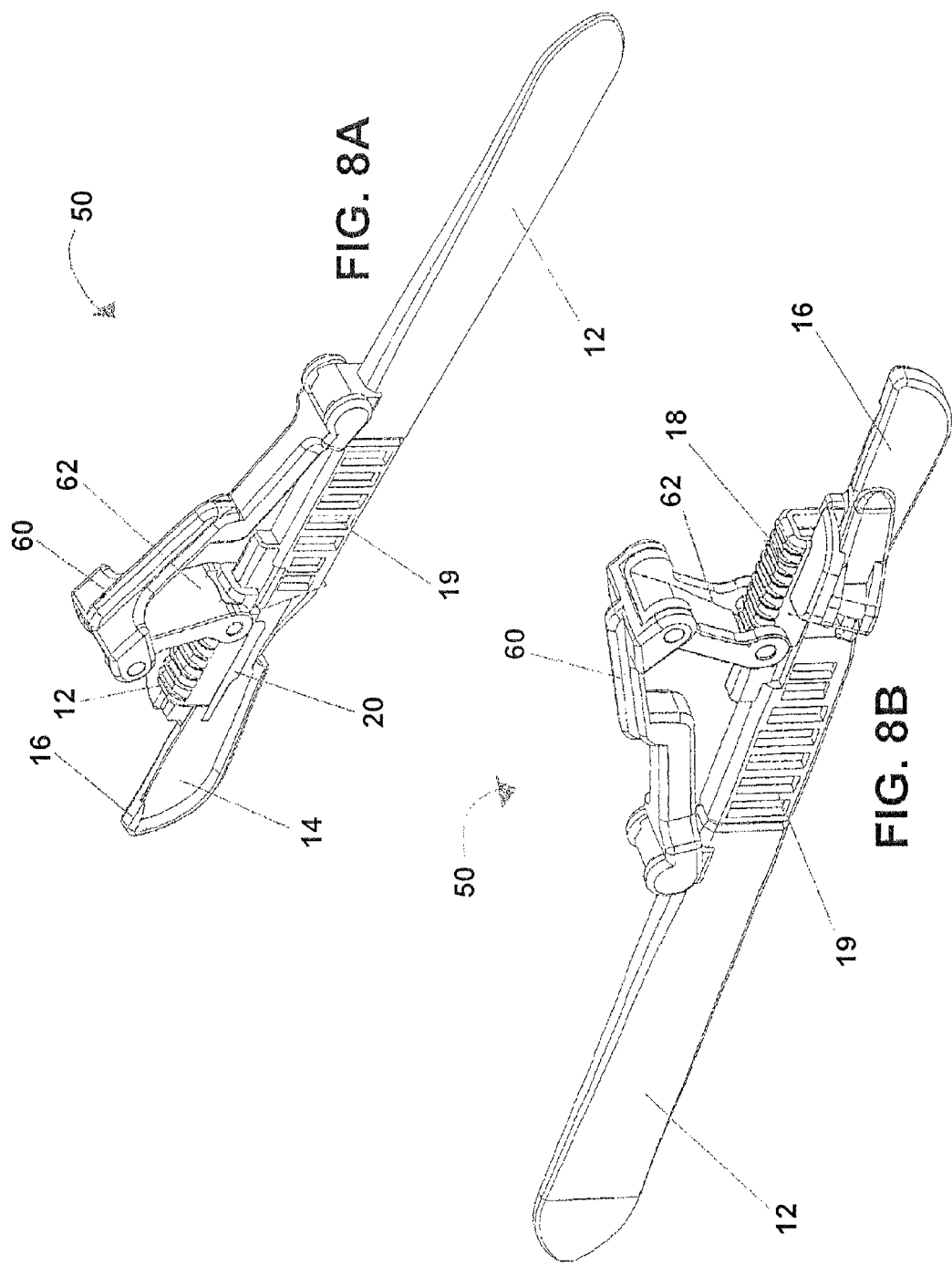

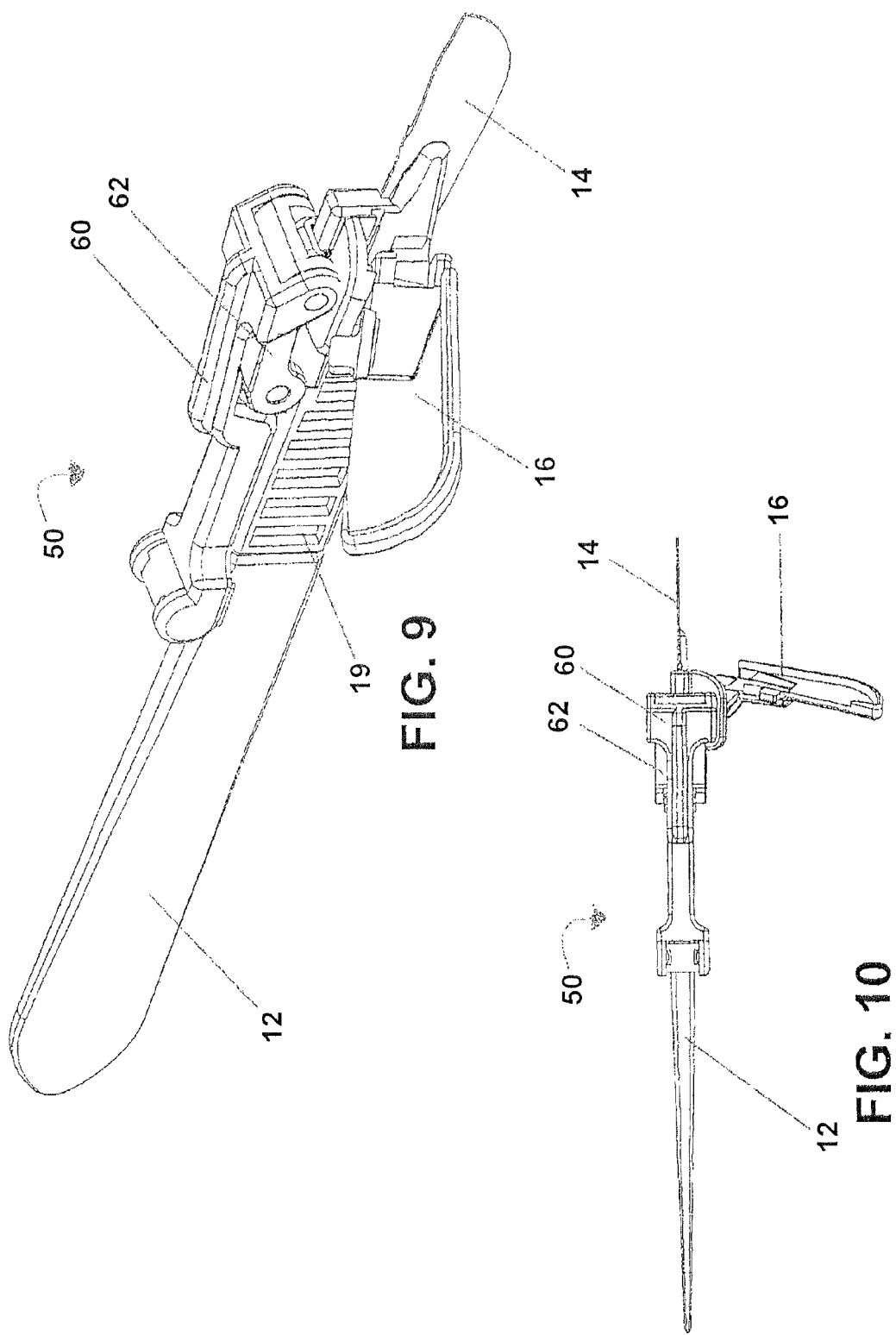

SHIELDED SCALPEL

FIELD OF THE INVENTION

The present invention relates to a surgical scalpel. More particularly, the present invention relates to a surgical scalpel having a retractable blade guard to protect against inadvertent cuts during a surgical procedure.

BACKGROUND OF THE INVENTION

Surgical scalpels are a class of knives which are manufactured in accordance with particular stringent standards, in order to assure their quality and precision of handling. It goes without saying that the blade of the knife should be sharp and of fine quality, but the entire instrument should be of such a weight and size as to fit well and be comfortable within the hand of the surgeon. In addition, it should normally be well-balanced, be capable of precise manipulation, and it should be small enough so as not to obstruct the surgeon's view of the blade while in use.

In the sometimes harried atmosphere of an operating room, a surgeon must often work quickly, handing instruments back and forth to assistants. With sharp implements, such as scalpels, the danger of accidental cutting or jabbing of operating room personnel is ever present. The Needlestick Safety and Prevention Act passed by the United States Congress and signed into law on Nov. 6, 2000 addresses these hazards and provides the needed momentum to advance the design of commonly used but potentially injurious instruments. The Centers for Disease Control estimates that health care workers sustain more than 600,000 injuries each year through the utilization of sharp implements. Furthermore, certain infections, such as the AIDS virus can be transferred to individuals through minor cuts, when even small quantities of blood are mixed.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard for instance, by turning a threaded screw. Although such a blade guard could be used effectively prior to starting and after completing a surgical procedure, the guard could normally not be used and would be of no value during the procedure itself. Furthermore, even if the surgeon were able to use both hands, the scalpel would be unacceptable because the surgeon's attention is distracted from the procedure whenever handling the scalpel. In addition, the surgeon risks injuring oneself with the scalpel every time he needs to bring his second hand into use. Thus, this type of scalpel would be used in the open position during an entire surgical procedure and, for all intents and purposes, the blade guard is unavailable during the procedure.

Other prior art devices are shown to have spring loaded moving parts or tabs that clipped into notches on a hollow tubed sheathing device. These devices were not practical for surgical use because they did not provide a good grip or "feel" for the blade.

Based on the foregoing, it would be advantageous to provide an improved shielded scalpel readily adaptable for use during a variety of surgical procedures in a standard operating room and which overcomes at least one of the problems identified in the prior art shielded scalpels.

SUMMARY OF THE INVENTION

It is, therefore, an aspect of the present invention to provide a shielded scalpel. These and other advantages of the present invention are also accomplished by providing a scalpel comprising a handle having a front portion and a rear portion, a blade secured to the handle, wherein the blade and the handle are directed along an axis, a sliding assembly disposed on a portion of the handle, and a shield covering the blade, wherein movement of the sliding assembly causes the shield to rotate between a first position and a second position, wherein the blade is at least partially exposed.

It is another aspect of the present invention to provide a scalpel comprising a handle having a front portion and a rear portion, a blade secured to the handle, wherein the blade and the handle are directed along an axis, a sliding assembly disposed on a portion of the handle, and a shield covering the blade, wherein movement of the sliding assembly is selectively engaged to rotate the shield away from the blade between a first position, wherein the shield covers at least a portion of the blade, and a second position at an angle above a horizontal plane of the scalpel, wherein the blade is at least partially exposed.

Other aspects and advantages of the present invention will become apparent and obvious from a study of the following description and the accompanying drawings, which are merely illustrative of the invention.

BRIEF DESCRIPTION OF THE DRAWINGS

FIG. 2A is a perspective view of a first embodiment of a shielded scalpel in an blade-exposed open position in accordance with the present invention;

FIG. 2B is a front perspective view of FIG. 2 illustrating the inclined angle of the shield in the blade-exposed open position;

FIGS. 3A and 3B are side perspective views of the first embodiment of the present invention with the blade and shield removed from the scalpel;

FIGS. 8A and 8B are rear perspective views of the second embodiment of the present invention;

FIG. 9 is a front perspective view of the second embodiment of the present invention in the blade-exposed open position; and FIG. 10 is a top elevational view of FIG. 9.

DETAILED DESCRIPTION OF THE INVENTION

Figure 1:
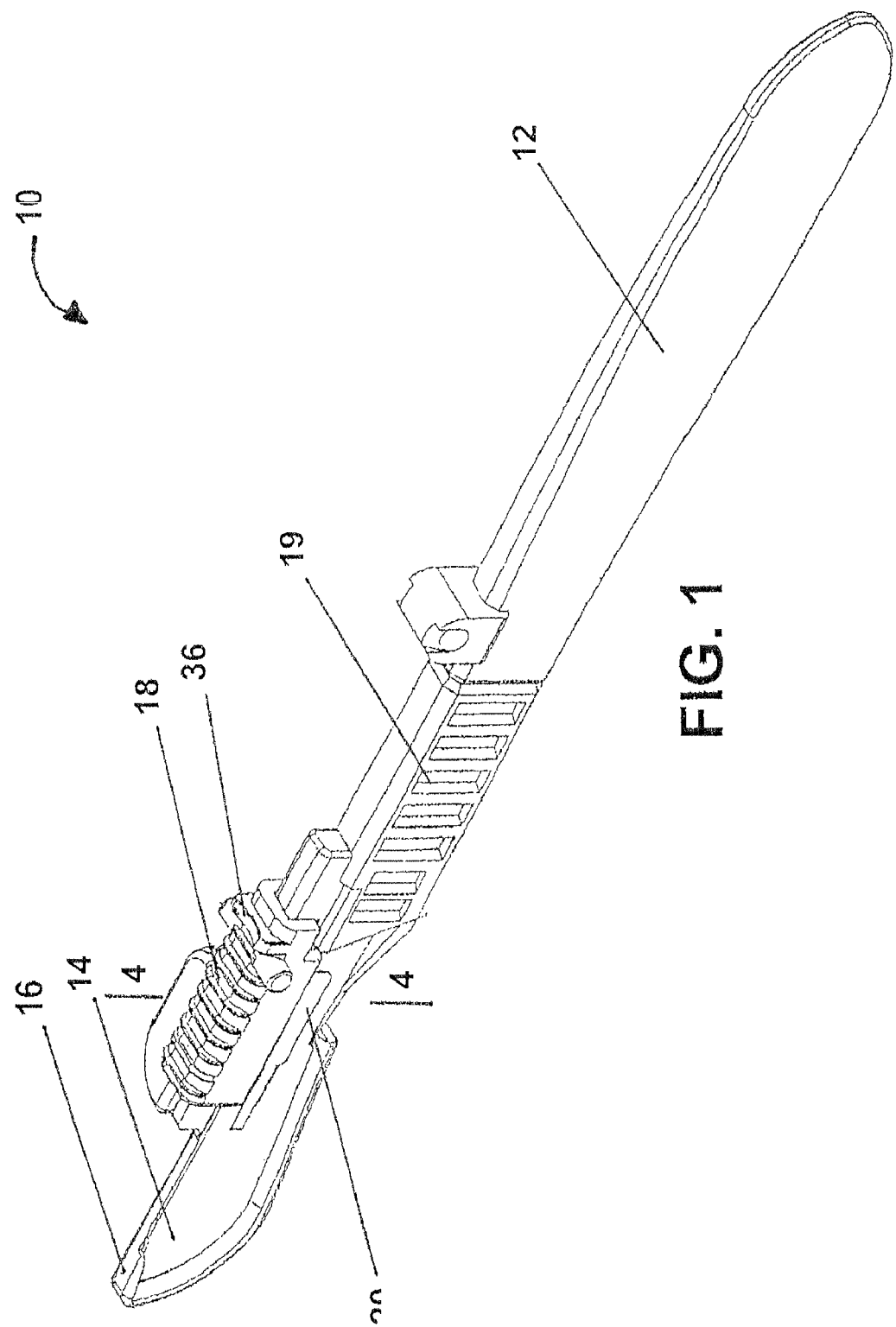
FIG. 1 is a perspective view of a first embodiment of a shielded scalpel in a blade-guarded closed position in accordance with the present invention.

As seen in FIGS. 1-9, the shielded scalpel of the present invention indicated generally at 10 is generally a scalpel commonly used during surgical procedures in a standard operating room with a shield that covers the blade when not in use. In one embodiment, scalpel 10 broadly includes a handle 12, a blade 14 detachably secured to handle 12, a shield 16 that is detachably connected to the handle and has a blade protecting edge that covers at least a portion of blade 14 when not in use, and a sliding assembly 18 disposed on a top portion of handle 12. Optionally, a plurality of grooves 19 are incorporated into handle 12 in an area where an operator holds scalpel 10 in normal use. Grooves 19 provide a surface where scalpel 10 is gripped and held, thus reducing the likelihood of scalpel 10 slipping out of the hand of an operator, i.e. surgeon or other medical professional, during a surgical procedure.

In use, scalpel 10 is operated by being held in the hand by an operator. An index finger is used to pull sliding assembly 18 towards the rear portion of handle 12. This rearward movement causes sliding assembly 18 to selectively engage shield 16, thus causing shield 16 to rotate away from the longitudinal axis of handle 12 and blade 14 from a first blade-guarded closed position to a second blade-exposed open position. As can be seen in FIG. 2A, when blade 14 is generally completely exposed in the open position, shield 16 does not impair the field of view of an operator when an incision is made. As seen in FIG. 2B, shield 16, when moved to the blade-exposed open position, is optionally maintained at an inclined angle above a horizontal plane of the bottom portion of scalpel 10 such that shield 16 is removed from the cutting surface of blade 14. In this embodiment, the inclined angle is greater than about 10°. Shield 16 is retained in the blade-exposed open position by maintaining rearward pressure on sliding assembly 18 with the index finger of the operator. Upon completing the use of scalpel 10, removing the pressure applied to sliding assembly 18 by the index finger is sufficient to return shield 16 to the blade-guarded closed position.

Figure 2C:
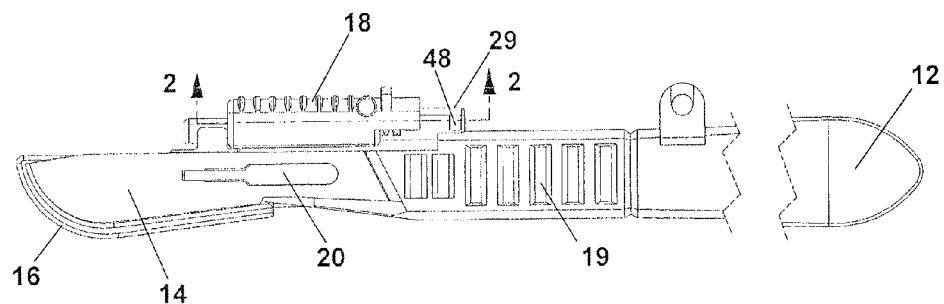
FIG. 2C is a side view of another embodiment of a shielded scalpel in a blade-guarded closed position in accordance with the present invention.
Figure 2D:
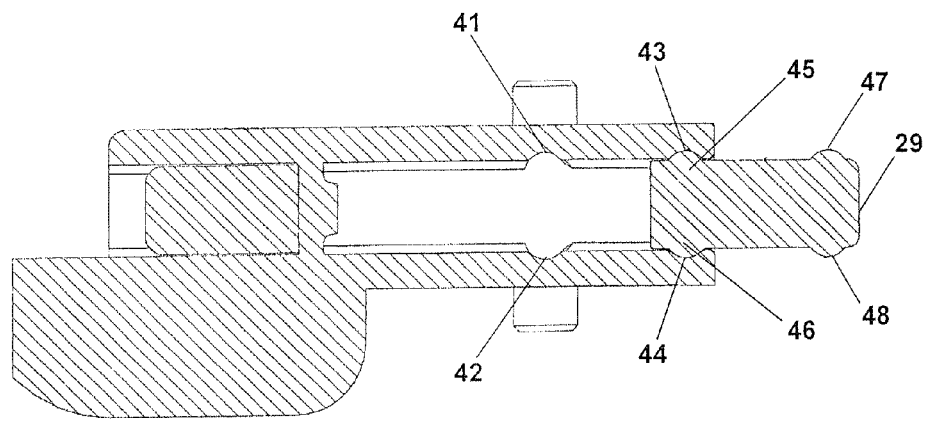
FIG. 2D is a cross-sectional view of another embodiment of the present invention across lines 2-2 of FIG. 2C.
Figure 4A:
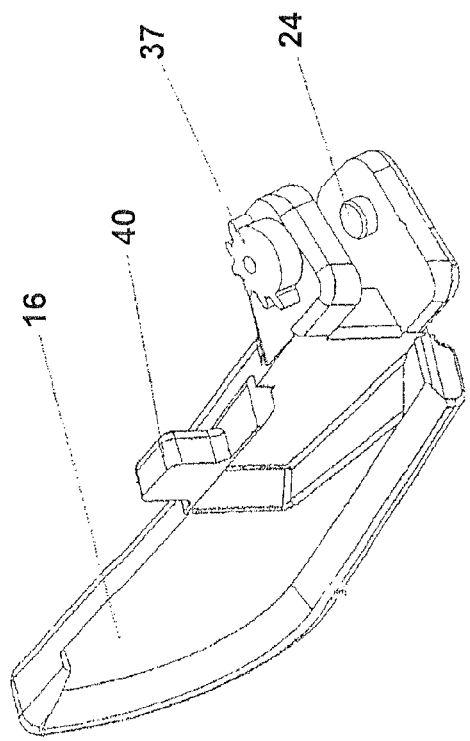
FIG. 4A is a side perspective view of the shield of FIG. 1.
Figure 4B:
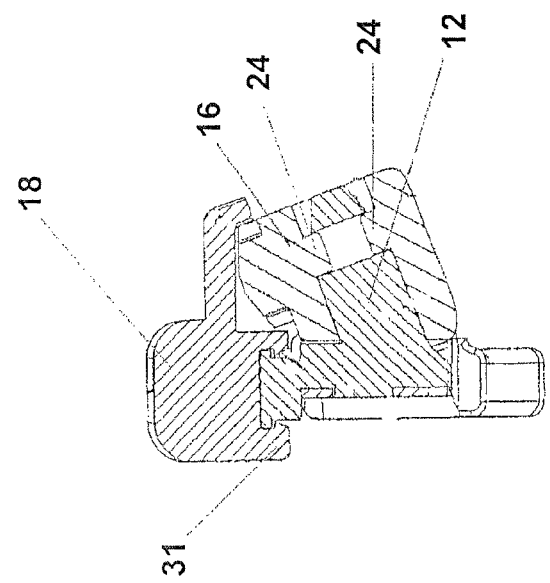
FIG. 4B is a cross-sectional view of the scalpel across lines 4-4 of FIG. 1.

In a further embodiments as seen in FIGS. 2C and 2D, the interior portion of sliding assembly 18 is manufactured with a plurality of grooves 41-44 and rear end support 29, located near the front portion of handle 12, is manufactured with a plurality of protrusions 45-48. Initially, while shield 16 is in the blade-guarded closed position, groove 43 engages protrusion 45 and groove 44 engages protrusion 46. In use, a finger is used to pull sliding assembly 18 towards the rear portion of handle 12. This rearward movement causes grooves 41-44 of sliding assembly 18 to selectively engage protrusions 45-48 found on rear end support 29 of handle 12. More specifically, groove 41 engages protrusion 45, groove 42 engages protrusion 46, groove 43 engages protrusion 47, and groove 44 engages protrusion 48. The engagement of grooves 41-44 with protrusions 45-48 provides a temporary secured position for sliding assembly 18 when shield 16 is in a blade-exposed open position. Upon completing the use of scalpel 10, sliding assembly 18 is pushed towards the front portion of handle 12. This forward movement disengages the protrusions 45-48 from grooves 41-44 in the blade-exposed open position and returns shield 16 to the blade-guarded closed position where groove 43 engages protrusion 45 and groove 44 engages protrusion 46. In a separate embodiment, protrusions 47-48 may be optionally omitted. This allows groove 43 to engage protrusion 45 and groove 44 to engage protrusion 46 when shield 16 is in the blade-guarded closed position. Similarly, when shield 16 is in the blade-exposed open position sliding assembly 18 can be temporarily secured when groove 41 engages protrusion 45 and groove 42 engages protrusion 46.

Reusable and disposable scalpels are considered in accordance with the present invention. In the case of a reusable scalpel, used blade 14 is replaced with a new blade after each surgical use. If deemed necessary, shield 16 and sliding assembly 18 may also be replaced after each surgical use when the reusable scalpel is used. With a disposable scalpel, the cutting blade as well as the scalpel is disposed of after each surgical use. In accordance with the present invention, handle 12 is preferably made of high quality stainless steel that is reusable, although it could equally well be made of any other material used for surgical knives including a plastic material that is disposable. Sliding assembly 18 and shield 16 are preferably made of resilient plastic material known to those skilled in the art, however, the use of stainless steel may also be considered for use in constructing shield 16 and sliding assembly 18. Sliding assembly 18 is slidably engaged with a top portion of handle 12. At its forward end, handle 12 is fashioned with a fitting 20 to detachably receive and retain blade 14. This fitting is preferably made so that blades of various shapes and sizes may be interchanged. When using a reusable steel scalpel, it is envisioned that sliding assembly 18 and shield 16 could be attached to the steel scalpel after sterilization.

As seen in FIGS. 3A and 3B, handle 12 has a boss 22 with an aperture therethrough located along the front side of scalpel 10 providing a source of attachment for shield 16 to handle 12. Boss 22 acts as a pivot point when shield 16 is detachably connected to handle 12. In the present invention, detachably connected refers to being connected in such a manner that separation under appropriate force, such as pressure generated by a hand, is facilitated. Preferably, the at least two sides of boss 22 are tapered to provide a positive lead-in for mounting portions 24 of shield 16 (see FIGS. 4A and 4B). Shield 16 is detachably connected to handle 12 by aligning pivot pins 24 of shield 16 with the tapered walls of boss 22, inserting mounting portions 24 into boss 22 such that shield 16 is releasably secured to handle 12. Although shield 16 is releasably secured to handle 12, free rotation about the pivot point of boss 22 is permitted thus allowing shield 16 to move between a blade-guarded closed position and a blade-exposed open position.

Figure 5:
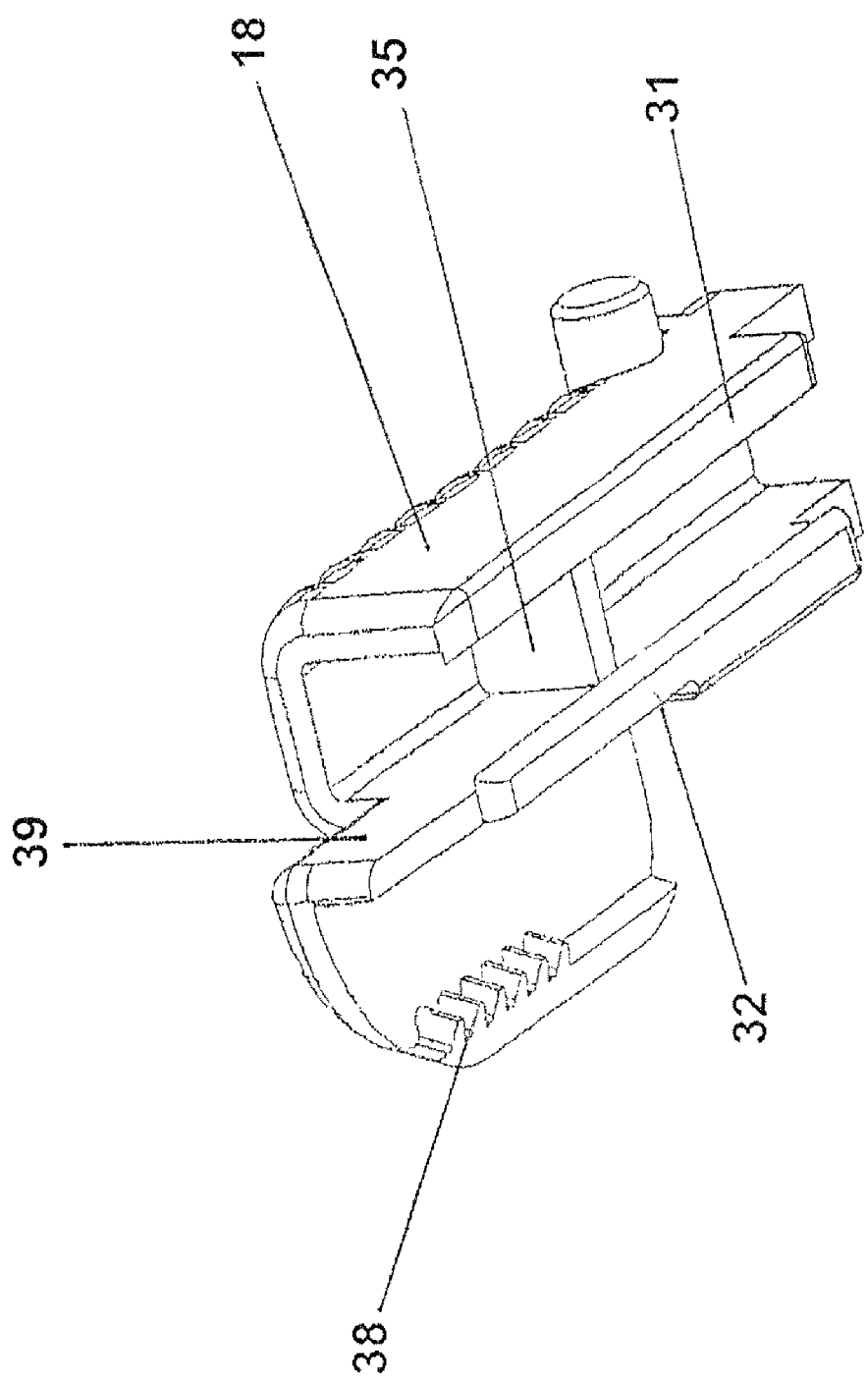
FIG. 5 is a bottom perspective view of the sliding assembly of FIG. 1.

As seen in FIGS. 3A and 3B, handle 12 includes a channel 26 located substantially near the front portion of handle 12. Channel 26 includes a base 27, a front end support 28 and a rear end support 29. Optionally, if grooves 41-44 and protrusions 45-48 of FIGS. 2C and 2D of the present invention are not provided, scalpel 12 may further include a means for returning the shield to a closed position, wherein the means is spring 30. Channel 26 houses slider return spring 30, wherein spring 30 is situated between front end support 28 and rear end support 29. A pair of assembly grooves 33 and 34 are located within handle 12 and beneath channel 26. Sliding assembly 18 is disposed onto handle 12 by placing sliding assembly 18 over channel 26 that houses spring 28. A means for holding sliding assembly on scalpel facilitates in retaining sliding assembly 18 on handle 12 during use. An example of the means for holding sliding assembly are represented by longitudinal securing assembly tabs 31 and 32 as seen in FIG. 5. Longitudinal securing assembly tabs 31 and 32 of sliding assembly 18 are received and become slidably engaged with assembly grooves 33 and 34. Assembly grooves 33 and 34 retain sliding assembly 18 to handle 12 and permit longitudinal movement along of sliding assembly 18 along handle 12.

Figure 6A:
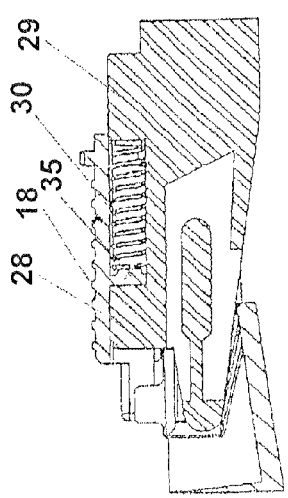
FIGS. 6A-6C are sectional views at different stages wherein the sliding assembly contacts and compresses the spring while the shield goes from a blade-guarded closed position to a blade-exposed open position.
Figure 6B:
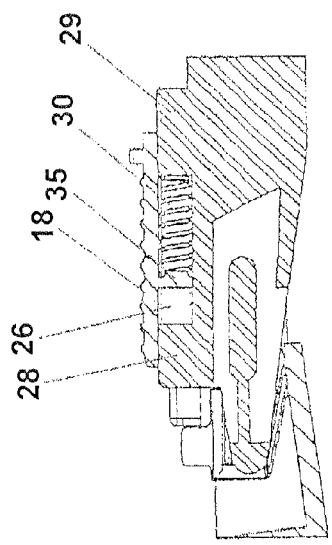
Figure 6C:
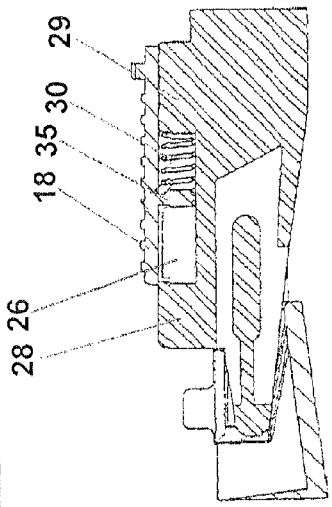

Prior to engaging longitudinal securing assembly tabs 31 and 32 with assembly grooves 33 and 34, it is necessary that return spring front support rib 35, located underneath sliding assembly 18, rest between the front end of spring 30 housed in channel 26 and front end support 28. FIGS. 6A-6C reveal that as sliding assembly 18 is pulled towards the rear end of handle 12, return front support rib 35 gradually compresses spring 30 against rear end support 29 of channel 26. As this movement is occurring, shield 16 is moved from the blade-guarded closed position to the blade-exposed open position. After completing use of scalpel 10, sliding assembly is released thereby permitting spring 30 to return to its initial, expanded state. As spring 30 decompresses, the front end portion of spring 30 engages and pushes return spring front support rib 35 of shield assembly 18 toward the front portion of handle 12. This forward movement of sliding assembly 18 concurrently moves shield 16 from the blade-exposed open position to the blade-guarded closed position. The uncoiling of spring 30 assures that sliding assembly 18 is fully returned and shield assembly 18 is secured in the blade-guarded closed position. It is noted that the above-mentioned spring-facilitated movement of shield assembly 18 from a blade-exposed open position to a blade-guarded closed position may be considered optional if grooves 41-44 of sliding assembly 18 and protrusions 45-48 of rear end support 29, as seen in FIGS. 2C and 2D, are provided.

Figure 7C:
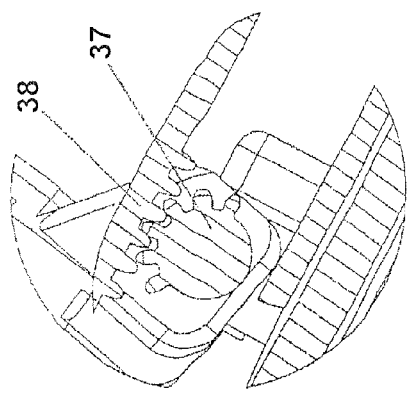
FIGS. 7A-7C are sectional views at different stages of engagement between the gear of the shield and the gear rack of the sliding assembly as the shield goes from a blade-guarded closed position to a blade-exposed open position.
Figure 7B:
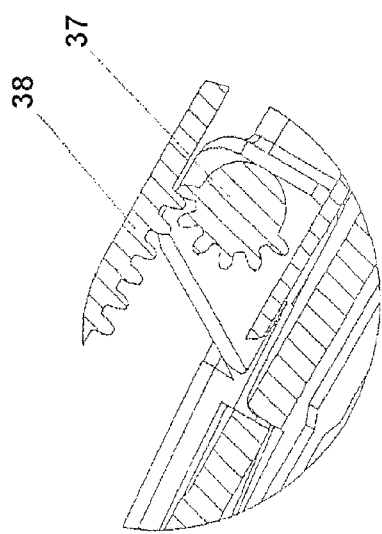
Figure 7A:
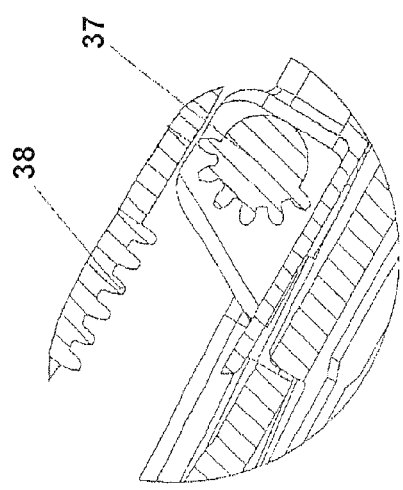

As shown in FIGS. 7A-7C, there are various stages of engagement between engaging element 37 and receiving element 38 which results in shield 16 going from a blade-guarded closed position to a blade-exposed open position. During normal operation, scalpel 10 is held in the hand of normal position of use except that the index finger of the operator rests on top of sliding assembly 18. Preferably, sliding assembly 18 includes at least one raised protrusion 17 providing a region the index finger can grasp during the movement of sliding assembly 18 as it is pulled towards the rear portion of handle 12. As shown in FIGS. 7A-7C, in the blade-guarded closed position of shield 16, there exists a first displacement, for example, of approximately 0.125 inches between engaging element 37 of shield 16 (see FIG. 4A) and receiving element 38 of sliding assembly 18 (see FIG. 3A). In one aspect of the present invention, engaging element 37 is a spur gear and receiving element 38 is a gear rack. This first displacement phase is considered to be the unlocking stage, wherein shield 16 remains in the blade-guarded closed position while extended locking rib 39 of sliding assembly 18 clears stop rib 40 of shield 16. Next, with continuing rearward movement, engaging element 37 and receiving element 38 contact one another initiating the gear engagement stage. In this stage, shield 16 becomes unlocked, but remains in the blade-guarded closed position. Further movement of sliding assembly 18 towards the rear portion of handle 12 by approximately another 0.125 inches begins the second displacement phase. During this phase, full engagement of engaging element 37 and receiving element 38 results in rotation of shield 16 about an axis generally transverse to the longitudinal axis of handle 12 and blade 14 from the blade-guarded closed position to the blade-exposed open position. In this example, the total sliding assembly displacement is approximately 0.250 inches. Alternatively, other engaging elements and receiving elements can be utilized to either shorten or lengthen the displacement distances encountered during the exposure of blade 14. Once shield 16 is in the blade-exposed open position, it remains in this position as long as the operator retains an index finger on finger grip 17 of sliding assembly 18 or sliding assembly 18 alone. When the index finger is released from finger grip 17 of sliding assembly 18 or sliding assembly 18 alone, spring 30 decompresses against return spring front support rib 35 forcing sliding assembly 18 towards the front portion of handle 12. This forward movement continues until extended locking rib 39 of sliding assembly 18 abuts against stop rib 40 of shield 16, therein releasably locking shield 16 in the blade-guarded closed position. The design, including the placement and size, of extended locking rib 39 and stop rib 40 can be modified so as to insure a desired degree of tightness is achieved between these two components.

Referring now to FIGS. 8-10, there is disclosed a second embodiment 50 of a scalpel in accordance with the present invention. In this embodiment, elements which are essentially the same as the corresponding elements in embodiment 10 are indicated with the same reference characters and will not be described any further. Scalpel 50 differs from scalpel 10 essentially in activation of the shield 16 movement. Actuating member 60 is detachably connected to handle 12 at one end and to a portion of linking member 62 at the other end. Linking member 62, in turn, is detachably connected to sliding assembly 18.

In use, scalpel 50 of the second embodiment of the present invention is operated similarly to the scalpel 10 of the first embodiment of the present invention by being held in the hand by an operator, i.e. surgeon or other medical professional, except instead of using the index finger to press on and pull sliding assembly 18 towards the rear portion of handle 12, the index finger of the operator is used to depress actuating member 60 which forces linking member 62 to move sliding assembly 18 towards the rear portion of handle 12. This movement causes sliding assembly 18 to selectively engage shield 16 causing shield 16 to rotate about an axis generally transverse to the longitudinal axis of handle 12 and blade 14 from a first blade-guarded closed position to a second blade-exposed open position. The mechanics of shield 16 opening and closing, as well as the positioning of shield 16 in the blade-exposed open position for scalpel 50 with use of actuating member 60 and linking member 62 will be essentially the same as described for scalpel 10.

In a further embodiment, as seen similarly in FIGS. 2C and 2D for scalpel 10, the interior portion of sliding assembly 18 of scalpel 50 is manufactured with a plurality of grooves 41-44 and rear end support 29, located near the front portion of handle 12, is manufactured with a plurality of protrusions 45-46. Initially, while shield 16 is in the blade-guarded closed position, groove 43 engages protrusion 45 and groove 44 engages protrusion 46. In use, as described above, an index finger of an operator is used to depress actuating member 60 which forces linking member 62 to move sliding assembly 18 towards the rear portion of handle 12. This rearward movement causes grooves 43-44 of sliding assembly 18 to selectively engage protrusions 45-46 found on rear end support 29 of handle 12. More specifically, groove 41 engages protrusion 45 and groove 42 engages protrusion 46. The engagement of grooves 43-44 with protrusions 45-46 provides a temporary secured position for sliding assembly 18 when shield 16 is in a blade-exposed open position. Upon completing the use of scalpel 50, actuating member 60 is slowly released by the index finger of the operator and can be gently pushed upward to disengage protrusion 45 from groove 41 and protrusion 46 from groove 42, ultimately returning shield 16 to the blade-guarded closed position wherein groove 43 engages protrusion 45 and groove 44 engages protrusion 46.

Based on the foregoing disclosure, it should be apparent that the shielded scalpel of the present invention will achieve the objectives set forth above. It is therefore understood that any evident variations will fall within the scope of the claimed invention. Thus, alternate specific component elements can be selected without departing from the spirit of the invention disclosed and described herein.

What is claimed is:

1. A scalpel comprising:
a handle having a front portion and a rear portion;
a blade secured to the handle, the blade having a direction of cut extending along the length of the handle, wherein the blade and the handle are aligned such that the blade and handle coincide along a common longitudinal axis, and a vertical plane passing through the common longitudinal axis of the blade and the handle and the direction of cut of the blade, and including a horizontal plane perpendicular to the vertical plane and passing through the common longitudinal axis of the blade and the handle;
a sliding assembly disposed on a portion of the handle; and
a shield covering the blade, wherein movement of the sliding assembly causes the shield to rotate between a first position covering the blade and a second position, wherein the blade is at least partially exposed, and wherein the shield is rotatable away from the vertical plane of the blade and the handle and along the horizontal plane when moved to the second position.

2. The scalpel of claim 1, further comprising a means for returning the shield to a closed position.

3. The scalpel of claim 2, wherein the means for returning is a spring.

4. The scalpel of claim 3 wherein the spring is housed within a channel of the handle, wherein the channel comprises a base, a front end support and a rear end support.

5. The scalpel of claim 1, wherein the sliding assembly further comprises a receiving element and the shield further comprises an engaging element such that when the engaging element couples with the receiving element, the shield is movable to the second position.

6. The scalpel of claim 5, wherein the receiving element is a gear rack and the receiving element is a rotatable gear.

7. The scalpel of claim 1, wherein the sliding assembly further comprises a means for holding the sliding assembly on the scalpel.

8. The scalpel of claim 1, wherein the shield has a blade protecting edge preventing access to the blade in the first position.

9. The scalpel of claim 1, wherein the shield is maintained in the second position at an inclined angle above the horizontal plane.

10. The scalpel of claim 1 further comprising:
an actuating assembly, wherein the actuating assembly provides movement of the shield relative to the blade.

11. The scalpel of claim 10, wherein the actuating assembly comprises an actuating member and a linking member, wherein the actuating member is detachably connected to the handle and a portion of the linking member, and wherein the linking member is detachably connected to the sliding assembly.

12. The scalpel of claim 10, wherein the shield is moved to the second position by depressing the actuating member of the actuating assembly.

13. The scalpel of claim 1, wherein the sliding assembly further comprises a plurality of grooves and a rear end support comprises a plurality of protrusions, wherein the protrusions are selectively engageable with the grooves which provide a temporary secured position for the sliding assembly when the shield is in the first or second position.

14. The scalpel of claim 1, wherein the scalpel is a reusable scalpel or a disposable scalpel.

15. A scalpel comprising:
a handle having a front portion and a rear portion;
a blade secured to the handle, the blade having a direction of cut extending along the length of the handle, wherein the blade and the handle are aligned such that the blade and handle coincide along a common longitudinal axis, and a vertical plane passing through the common longitudinal axis of the blade and the handle and the direction of cut of the blade, and including a horizontal plane perpendicular to the vertical plane and passing through the common longitudinal axis of the blade and the handle;
a sliding assembly disposed on a portion of the handle; and
a shield covering the blade, wherein movement of the sliding assembly is selectively engaged to rotate the shield away from the blade between a first position, wherein the shield covers at least a portion of the blade, and a second position, wherein the shield is rotatable away from the vertical plane of the blade and the handle and along the horizontal plane when moved to the second position and, wherein the blade is at least partially exposed.

16. The scalpel of claim 15, wherein the shield is maintained in the second position at an inclined angle above the horizontal plane.

17. The scalpel of claim 15, wherein the sliding assembly further comprises a plurality of grooves and a rear end support comprises a plurality of protrusions, wherein the protrusions are selectively engageable with the grooves which provides a temporary secured position for the sliding assembly when the shield is in the first or second position.

* * * * *